(12) United States Patent
Kulas et al.

(10) Patent No.: US 10,335,166 B2
(45) Date of Patent: Jul. 2, 2019

(54) SURGICAL BURS WITH DECOUPLED RAKE SURFACES AND CORRESPONDING AXIAL AND RADIAL RAKE ANGLES

(71) Applicant: Medtronic PS Medical, Inc., Fort Worth, TX (US)

(72) Inventors: John W. Kulas, Euless, TX (US); Donald E. Stearns, Fort Worth, TX (US)

(73) Assignee: MEDTRONICS PS MEDICAL, INC., Louisville, CO (US)

( * ) Notice: Subject to any disclaimer, the term of this patent is extended or adjusted under 35 U.S.C. 154(b) by 315 days.

(21) Appl. No.: 14/664,258

(22) Filed: Mar. 20, 2015

(65) Prior Publication Data
US 2015/0297243 A1 Oct. 22, 2015

Related U.S. Application Data

(60) Provisional application No. 61/980,102, filed on Apr. 16, 2014.

(51) Int. Cl.
*A61B 17/16* (2006.01)
*B23C 5/10* (2006.01)

(52) U.S. Cl.
CPC ...... *A61B 17/1615* (2013.01); *A61B 17/1695* (2013.01); *B23C 5/1009* (2013.01); *B23B 2251/00* (2013.01); *B23C 2210/0407* (2013.01); *B23C 2210/0428* (2013.01); *B23C 2210/0457* (2013.01)

(58) Field of Classification Search
CPC ............ A61B 17/1695; A61B 17/1615; B23B 2215/046
See application file for complete search history.

(56) References Cited

U.S. PATENT DOCUMENTS

| | | | |
|---|---|---|---|
| 180,554 A | 8/1876 | Cubberley | |
| 372,400 A | 11/1887 | Browne | |
| 533,573 A | 2/1895 | Wilkens | |
| 1,309,706 A * | 7/1919 | Taylor | ................... B23B 51/02 408/230 |
| 2,795,979 A | 6/1957 | Zerwick | |
| 2,847,895 A | 8/1958 | Wagner | |
| 2,903,922 A | 9/1959 | Ernst | |
| 3,387,511 A | 6/1968 | Ackart, Sr. | |
| 3,872,594 A | 3/1975 | Gerteisen | |
| 3,937,222 A | 2/1976 | Banko | |

(Continued)

FOREIGN PATENT DOCUMENTS

| | | |
|---|---|---|
| CN | 101745679 A | 6/2010 |
| CN | 201565651 U | 9/2010 |

(Continued)

OTHER PUBLICATIONS

Find Your Perfect Balance. Midas Rex Legend 7.5. cm Attachments and Tools. Medtronic brochure. (2012) 3 pages.

(Continued)

*Primary Examiner* — Olivia C Chang
(74) *Attorney, Agent, or Firm* — Harness Dickey

(57) ABSTRACT

A surgical bur including flutes and lands. Each of the flutes includes a cutting edge, rake surfaces and a clearance surface. The rake surfaces of one of the flutes are decoupled from each other. Each of the lands is disposed between a pair of the flutes.

43 Claims, 5 Drawing Sheets

(56) References Cited

U.S. PATENT DOCUMENTS

| | | | |
|---|---|---|---|
| 4,445,509 A | 5/1984 | Auth | |
| 4,594,034 A | 6/1986 | Maier | |
| 4,600,006 A | 7/1986 | Baker | |
| 4,602,900 A | 7/1986 | Arpaio, Jr. et al. | |
| 4,699,550 A | 10/1987 | Baker | |
| 4,740,121 A | 4/1988 | Arnold | |
| 4,803,982 A | 2/1989 | Baker | |
| 4,951,690 A | 8/1990 | Baker | |
| 4,975,003 A | 12/1990 | Hosoi | |
| 4,978,350 A | 12/1990 | Wagenknecht | |
| 5,007,911 A | 4/1991 | Baker | |
| 5,011,342 A | 4/1991 | Hsu | |
| 5,122,134 A | 6/1992 | Borzone et al. | |
| 5,143,490 A | 9/1992 | Kopras | |
| 5,190,548 A | 3/1993 | Davis | |
| 5,209,612 A | 5/1993 | Kish | |
| 5,236,291 A | 8/1993 | Agapiou et al. | |
| 5,302,059 A | 4/1994 | Fabiano | |
| 5,429,504 A | 7/1995 | Peltier et al. | |
| 5,467,837 A | 11/1995 | Miller et al. | |
| 5,514,141 A | 5/1996 | Prizzi, Jr. | |
| 5,575,650 A | 11/1996 | Niznick et al. | |
| 5,579,185 A | 11/1996 | Tsai et al. | |
| D378,780 S | 4/1997 | Shuler | |
| 5,618,293 A | 4/1997 | Sample et al. | |
| 5,658,305 A | 8/1997 | Baker | |
| 5,810,517 A | 9/1998 | Bostic | |
| 5,833,402 A | 11/1998 | Martin | |
| 5,846,035 A | 12/1998 | Karafillis et al. | |
| 5,855,581 A | 1/1999 | Koblish et al. | |
| 5,913,867 A | 6/1999 | Dion | |
| 5,964,553 A | 10/1999 | Blomberg et al. | |
| 5,980,525 A | 11/1999 | Bryant et al. | |
| 6,068,632 A | 5/2000 | Carchidi et al. | |
| 6,132,448 A | 10/2000 | Perez et al. | |
| 6,238,398 B1 | 5/2001 | Lechot | |
| 6,258,093 B1 | 7/2001 | Edwards et al. | |
| 6,332,886 B1 | 12/2001 | Green et al. | |
| 6,431,801 B2 | 8/2002 | Vasudeva et al. | |
| 6,435,780 B1 | 8/2002 | Flynn | |
| 6,511,493 B1 | 1/2003 | Moutafis et al. | |
| 6,514,258 B1 | 2/2003 | Brown et al. | |
| 6,547,495 B2 | 4/2003 | Meece et al. | |
| 6,562,046 B2 | 5/2003 | Sasso | |
| 6,579,298 B1 | 6/2003 | Bruneau et al. | |
| 6,783,533 B2 | 8/2004 | Green et al. | |
| 7,520,703 B2 | 4/2009 | Rompel | |
| 7,862,263 B2 | 1/2011 | van Iperen | |
| 8,414,228 B2 | 4/2013 | Wells et al. | |
| 8,460,298 B2 | 6/2013 | O'Donoghue | |
| 9,179,923 B2 | 11/2015 | Gubellini et al. | |
| 9,232,952 B2 | 1/2016 | Kulas et al. | |
| 2003/0097133 A1 | 5/2003 | Green et al. | |
| 2004/0057803 A1 | 3/2004 | Walrath | |
| 2005/0203526 A1 | 9/2005 | Ellis | |
| 2005/0272004 A1 | 12/2005 | Desrosiers | |
| 2005/0273107 A1 | 12/2005 | Stevens | |
| 2005/0283160 A1 | 12/2005 | Knisely et al. | |
| 2006/0045639 A1 | 3/2006 | Flynn et al. | |
| 2006/0067797 A1 | 3/2006 | Calamia | |
| 2006/0085005 A1 | 4/2006 | Kenealy et al. | |
| 2006/0142775 A1 | 6/2006 | Heneberry et al. | |
| 2006/0269372 A1* | 11/2006 | Goshima | B23B 51/02 408/230 |
| 2007/0010822 A1 | 1/2007 | Zalenski et al. | |
| 2007/0160437 A1 | 7/2007 | Shultz et al. | |
| 2007/0163416 A1 | 7/2007 | Burgess | |
| 2007/0280792 A1 | 12/2007 | Kochan et al. | |
| 2008/0132929 A1 | 6/2008 | O'Sullivan et al. | |
| 2008/0140078 A1 | 6/2008 | Nelson et al. | |
| 2008/0167653 A1 | 7/2008 | Watlington et al. | |
| 2008/0177294 A1 | 7/2008 | O'Neil et al. | |
| 2008/0193234 A1 | 8/2008 | Davancens et al. | |
| 2008/0215148 A1 | 9/2008 | Lesinski et al. | |
| 2009/0023988 A1 | 1/2009 | Korner et al. | |
| 2009/0024129 A1 | 1/2009 | Gordon et al. | |
| 2009/0048602 A1 | 2/2009 | O'Donoghue | |
| 2009/0138015 A1 | 5/2009 | Conner et al. | |
| 2009/0216235 A1 | 8/2009 | Ellis | |
| 2009/0222009 A1 | 9/2009 | Ellis | |
| 2009/0264888 A1 | 10/2009 | Neumeyer et al. | |
| 2010/0054884 A1 | 3/2010 | Masuda et al. | |
| 2010/0057087 A1 | 3/2010 | Cha | |
| 2010/0121365 A1 | 5/2010 | O'Sullivan et al. | |
| 2010/0145341 A1 | 6/2010 | Ranck et al. | |
| 2010/0178631 A1 | 7/2010 | Gordils Wallis et al. | |
| 2010/0209200 A1 | 8/2010 | Delacretaz | |
| 2010/0286695 A1 | 11/2010 | Hannani et al. | |
| 2011/0015634 A1 | 1/2011 | Smith et al. | |
| 2011/0054884 A1 | 3/2011 | Drakwall et al. | |
| 2011/0098710 A1 | 4/2011 | Spratt et al. | |
| 2011/0112540 A1 | 5/2011 | McLean et al. | |
| 2011/0208194 A1 | 8/2011 | Steiner et al. | |
| 2011/0211922 A1 | 9/2011 | Maeda et al. | |
| 2011/0238070 A1 | 9/2011 | Santangelo et al. | |
| 2011/0238099 A1 | 9/2011 | Loreth | |
| 2012/0063860 A1* | 3/2012 | Wada | B23B 51/00 408/229 |
| 2012/0150209 A1 | 6/2012 | Gubellini et al. | |
| 2012/0158125 A1 | 6/2012 | O'Sullivan et al. | |
| 2012/0330315 A1 | 12/2012 | Ranck et al. | |
| 2013/0028677 A1* | 1/2013 | Schwaegert | B23B 51/02 408/229 |
| 2013/0051937 A1 | 2/2013 | Volokh et al. | |
| 2013/0274779 A1 | 10/2013 | Kulas et al. | |
| 2014/0058423 A1 | 2/2014 | Smith et al. | |
| 2015/0025559 A1 | 1/2015 | Kulas et al. | |
| 2015/0297243 A1 | 10/2015 | Kulas et al. | |

FOREIGN PATENT DOCUMENTS

| | | |
|---|---|---|
| DE | 19826276 C1 | 11/1999 |
| EP | 1872739 A1 | 1/2008 |
| EP | 2561822 A2 | 2/2013 |
| JP | H06155126 A | 6/1994 |
| JP | 10-263914 | 10/1998 |
| JP | H10-263914 A | 10/1998 |
| JP | 2003291024 A | 10/2003 |
| JP | 2005125465 A | 5/2005 |
| JP | 2010-510042 A | 4/2010 |
| JP | 2013527781 A | 7/2013 |
| WO | WO-2007010389 A1 | 1/2007 |
| WO | WO-2008061711 A2 | 5/2008 |
| WO | WO-2008064350 A2 | 5/2008 |
| WO | WO-2010061933 A1 | 6/2010 |
| WO | WO-2011023381 A1 | 3/2011 |
| WO | WO-2011132876 A2 | 10/2011 |
| WO | WO-2012083468 A1 | 6/2012 |
| WO | WO-2014037518 A1 | 3/2014 |
| WO | WO-2015160884 A1 | 10/2015 |

OTHER PUBLICATIONS

Table of Contents, RedLine Tools catalog, www.redlinetools.com/Images/PDFs/Redline09/RL062009_Sec1_Front%20pl-9_72.pdf, pp. 1-8.

Innovations 2005 catalog, Komet GEBR. Brasseler GmbH & Co., KG, Lemgo, Germany, 28 pages.

Komet Burs mini catalogue 2007, Henry Schein Halas, www.henryschein.com.au, 19 pages.

Komet Surgery catalog, Mar. 2011, 8 pages.

Stryker Neuro Spine ENT brochure, Zyphr Burs, Kalamazoo, Michigan, www.stryker.com, 2011, 6 pages.

International Search Report and Written Opinion dated Aug. 28, 2013 for PCT/US2013/036269, claiming priority to U.S. Appl. No. 13/447,372, filed Apr. 16, 2012.

International Preliminary Report on Patentability and Written Opinion dated Oct. 30, 2014 for PCT/US2013/036269, claiming priority to U.S. Appl. No. 13/447,372, filed Apr. 16, 2012.

End Mill and Cutting Tool Design Criteria and Technical Features. Melin Tool Company. Retrieved from <http://www.endmill.com/pages/training/design.html on Jun. 14>, 2013. (pp. 1-4).

(56) References Cited

OTHER PUBLICATIONS

International Search Report and Written Opinion dated Oct. 10, 2014 for PCT/US2014/046827 claiming benefit of U.S. Appl. No. 13/944,650, filed Jul. 17, 2013.
Japanese Office Action dated Nov. 10, 2015 for Japanese Application No. 2015-507064 claiming benefit of PCT/US2014/046827 claiming benefit of U.S. Appl. No. 13/944,650, filed Jul. 17, 2013.
European Office Action dated Dec. 15, 2015 for European Application No. 13720176.0-1654 claiming benefit of PCT/US2013/036269.
Canadian Office Action dated Sep. 29, 2015 for Canadian Application No. 2,870,689 claiming benefit of PCT/US2013/036269.
Australian Office Action dated Jun. 23, 2015 for AU Application No. 2013249626 for PCT/US2013/036269 which claims benefit of U.S. Appl. No. 13/447,372, filed Apr. 16, 2012.
Canadian Office Action dated Aug. 4, 2016 for CA Application No. 2870689 for PCT/US2013/036269 which claims benefit of U.S. Appl. No. 13/447,372, filed Apr. 16, 2012.
Korean Office Action dated Mar. 16, 2016 for KR Application No. 10-2014-7031869 for PCT/US2013/036269 which claims benefit of U.S. Appl. No. 13/447,372, filed Apr. 16, 2012 with English translation.
Korean Office Action dated Sep. 30, 2016 for Korean Application No. 10-2014-7031869 corresponding to PCT/US2013/036269 which claims benefit of U.S. Appl. No. 13/447,372, filed Apr. 16, 2012 with English translation.
International Preliminary Report on Patentability dated Oct. 27, 2016 for Application No. PCT/US2015/025867 filed Apr. 15, 2015.
International Search Report and Written Opinion dated Jan. 3, 2017 for PCT/US2016/049464 claiming benefit of U.S. Appl. No. 14/840,217, filed Aug. 31, 2015.
International Search Report and Written Opinion dated Oct. 22, 2015 corresponding to PCT/US2015/025867 filed Apr. 15, 2015.
Australian Office Action dated Mar. 15, 2017 for AU Application No. 2015247768.
Canadian Office Action dated May 1, 2017 for CA Application No. 2,917,601.
Chinese Office Action (English translation) dated May 24, 2016 for Chinese Application No. 2013800311659 which claims benefit of PCT/2013/036269 filed Apr. 12, 2013.
International Preliminary Report on Patentability and Written Opinion dated Jan. 19, 2016 for PCT/US2014/046827, claiming priority to U.S. Appl. No. 13/944,650, filed Jul. 17, 2013.
Japanese Office Action dated Jun. 21, 2016 for Japanese Application No. 2015-50764 claiming benefit of PCT/US2013/036269 claiming benefit of U.S. Appl. No. 13/447,372, filed Apr. 12, 2013 with English translation.
International Search Report and Written Opinion dated Jul. 25, 2016 for PCT/US2016/023349 which claims benefit the benefit of U.S. Appl. No. 14/674,002, filed Mar. 31, 2015.
European Office Action dated Jul. 27, 2017 in corresponding European Application No. 14747254.2.
International Preliminary Report on Patentability dated Oct. 12, 2017 in corresponding/related International Application No. PCT/US2016/023349.
Canadian Office Action dated Aug. 22, 2017 in corresponding/related Canadian Application No. 2,945,806.
Extended European Search Report dated Jul. 3, 2017 in corresponding European Application No. 17151461.5.
Canadian Office Action dated Feb. 2, 2018 in corresponding/related Canadian Application No. 2,917,601.
Australian Office Action dated Mar. 21, 2018 in corresponding/related Australian Application No. 2016234968.
Japanese Office Action dated Apr. 19, 2018 in corresponding/related Japanese Application No. 2016-527065.
International Preliminary Report on Patentability dated Mar. 15, 2018 in corresponding/related International Application No. PCT/US2016/049464.
Australian Office Action dated Apr. 12, 2018 in corresponding/related Australian Application No. 2014290106.
Korean Office Action dated Feb. 19, 2018 in corresponding/related Korean Application No. 10-2016-7031697.
Office Action dated Jan. 7, 2019 in corresponding/related European Application No. 18191962.2.
Korean Office Action dated Dec. 7, 2018 in corresponding/related Chinese Application No. 10-2017-7031086.
Korean Office Action dated Jul. 12, 2018 in corresponding/related Korean Application No. 10-2016-7031697.
Canadian Office Action dated Jun. 7, 2018 in corresponding/related Canadian Application No. 2,945,806.
Chinese Office Action dated Nov. 6, 2018 in corresponding/related Chinese Application No. 201710146560.1.
Office Action dated Mar. 1, 2019 in corresponding Canadian Application No. 2,945,806.

* cited by examiner

SURGICAL BURS WITH DECOUPLED RAKE SURFACES AND CORRESPONDING AXIAL AND RADIAL RAKE ANGLES

CROSS-REFERENCE TO RELATED APPLICATIONS

This application claims benefit of U.S. Provisional Application No. 61/980,102 filed on Apr. 16, 2014. The disclosure of the above application is incorporated herein by reference.

FIELD

The disclosure relates to a surgical systems for bone cutting or shaping, and more particularly to surgical burs.

BACKGROUND

This section provides background information related to the present disclosure which is not necessarily prior art.

Surgical burs need sharp and durable cutting edges in order to efficiently dissect, cut and/or shape bone during a surgical procedure. Human anatomy tends to locate sensitive soft tissue structures, such as nerves and blood vessels, near bones for protection. These structures can include the dura mater. Dura mater, or dura, refers to the outermost layer of protective soft tissue surrounding the brain and spinal column of a patient. During cranial and spinal procedures, the distal end of a bur can come in contact with dura mater. The term "distal" means furthest away from a medical practitioner holding a surgical tool with a rotating bur. The term "proximal" means towards the medical practitioner and away from the patient.

It is desirable for the surgical burs to provide stability while drilling in an axial direction and to be able to efficiently cut while being moved in a radial direction. The axial direction may be, for example, a direction parallel to, along, and/or in line with a longitudinal axis of the surgical bur. The radial direction may be, for example, a direction away from and not parallel to the longitudinal axis of the surgical bur. The radial direction may be a direction away from and/or perpendicular to the longitudinal axis.

SUMMARY

This section provides a general summary of the disclosure, and is not a comprehensive disclosure of its full scope or all of its features.

A surgical bur is provided and includes flutes and lands. Each of the flutes includes a cutting edge, rake surfaces, and a clearance surface. The rake surfaces of one of the flutes are decoupled from each other. The rake surfaces of each of the flutes may be decoupled from each other. Each of the lands is disposed between a pair of the flutes.

In other features, a surgical bur is provided and includes flutes and lands. Each of the flutes includes a cutting edge, rake surfaces, and a clearance surface. The rake surfaces of one of the flutes includes (i) a first rake surface having a first rake angle, and (ii) a second rake surface having a second rake angle. Each of the flutes may have multiple rake surfaces with respective rake angles. The second rake angle is decoupled from the first rake angle. Each of the lands is disposed between a pair of the flutes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
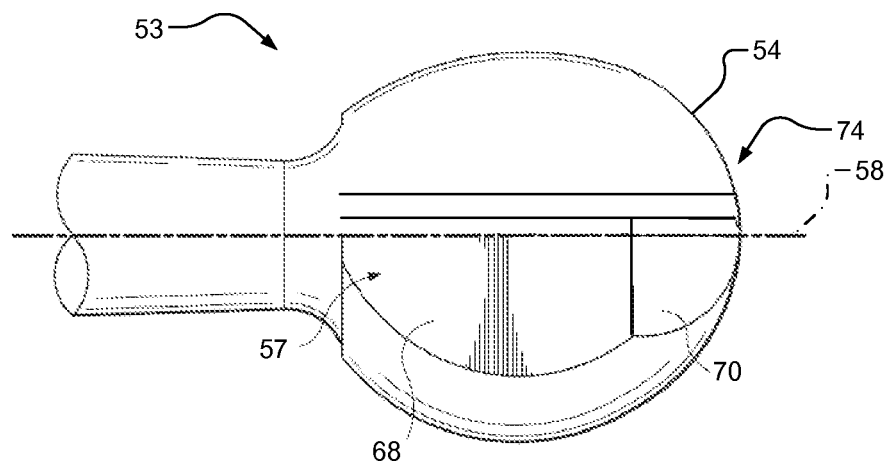
FIG. 1 is a side view of a dissection tool.
Figure 2:
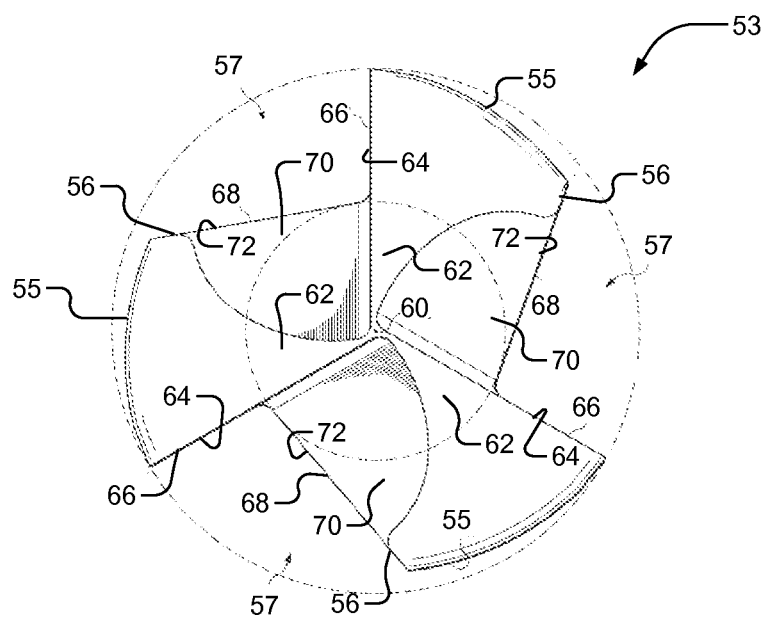
FIG. 2 is a perspective view of the dissection tool of FIG. 1.

FIGS. 1-2 show side and perspective views of a predicate dissection tool 53 including a surgical bur 54. The surgical bur 54 includes three convex lands 55 and three flutes 56. Each of the flutes 56 is located between the lands 55 and has a corresponding chip space 57. The lands 55 are equally spaced about a longitudinal axis 58 of the surgical bur 54. Distal portions 62 of the lands 55 are referred to as axial relief surfaces, which are convex-shaped. The axial relief surfaces 62 are not distinct from the lands 55 because: the lands 55 and the axial relief surfaces 62 are both convex-shaped (or have the same type of surface); and the axial relief surfaces 62 are continuous with the lands 55 without transitional surfaces or borders between the axial relief surfaces 62 and the lands 55.

The flutes 56 are also equally spaced about the longitudinal axis 58. Each of the flutes 56 has a single rake face 64 with a cutting edge 66 and a clearance surface 68. Each of the clearance surfaces 68 includes a distal portion (or surface) and a proximal portion (or surface). The distal portions of the clearance surfaces 68 are identified by numerical designator 70. The proximal portions of the clearance surfaces 68 are identified by numerical designator 72.

The efficiencies and stability of surgical bur 54 are constrained by the single rake surface 64 found on each flute. The placement of the rake surface 64 influences the entirety of the flute and the corresponding cutting edge 66. As manifested, the rake surface 64 is parallel to the longitudinal axis 58 and past a center point 60 (to the left of and not in alignment with the longitudinal axis as viewed from the distal end of the surgical bur 54). As a result, the surgical bur 54 has a neutral axial rake angle and a positive radial rake angle.

Surgical burs may have rake surfaces with (i) axial rake angles that are positive or negative, and (ii) radial rake angles that vary along cutting edges of corresponding flutes relative to locations along the cutting edges. The radial rake angle of a rake surface may be neutral (i.e. 0°) at a point where the rake surface crosses a plane through a longitudinal axis of the corresponding surgical bur. Examples of surgical burs having flutes that each includes multiple axial and radial rake angles are disclosed below.

The following description discloses rotatable surgical burs (referred to below as the surgical burs). The surgical burs include decoupled rake surfaces (may be referred to as rake faces) per flute and corresponding axial rake angles and radial rake angles. A negative axial rake angle may improve drilling stability of the surgical burs. A positive radial rake angle may increase cutting efficiency of the surgical burs.

Example embodiments will now be described more fully with reference to the accompanying drawings. The following description is merely exemplary in nature and is not intended to limit the present disclosure, application, or uses. It should be understood that throughout the drawings, corresponding reference numerals indicate like or corresponding parts and features.

Figure 3:
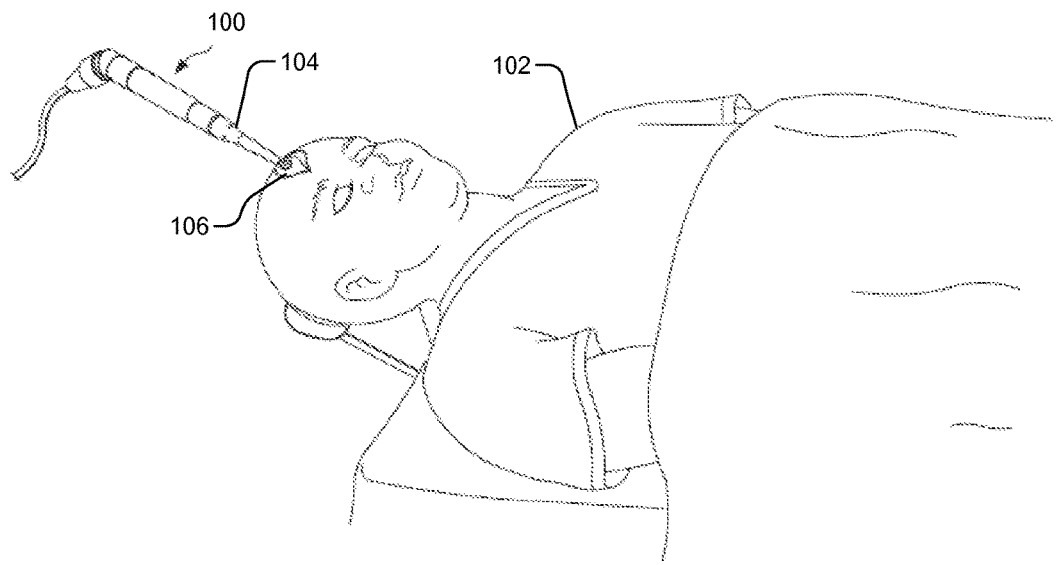
FIG. 3 is a perspective view of a surgical dissection cutter assembly incorporating a bur and in use on a patient in accordance with an embodiment of the present disclosure.

FIG. 3 shows a surgical dissection cutter assembly 100 incorporating a rotating surgical bur in use on a patient 102. The patient is undergoing a neurological operation. Access to the brain or other neurological structures often requires delicate dissection of bone and other tissues. FIG. 3 is provided for example purposes only, the surgical burs disclosed herein may be used in different tools and/or cutter assemblies and may be used for other procedures and/or operations. The dissection cutter assembly 100 includes a dissection tool driver 104, which is being utilized to dissect a portion of bone and adjacent tissue of the patient 102 in the surgical access site 106.

Figure 4:
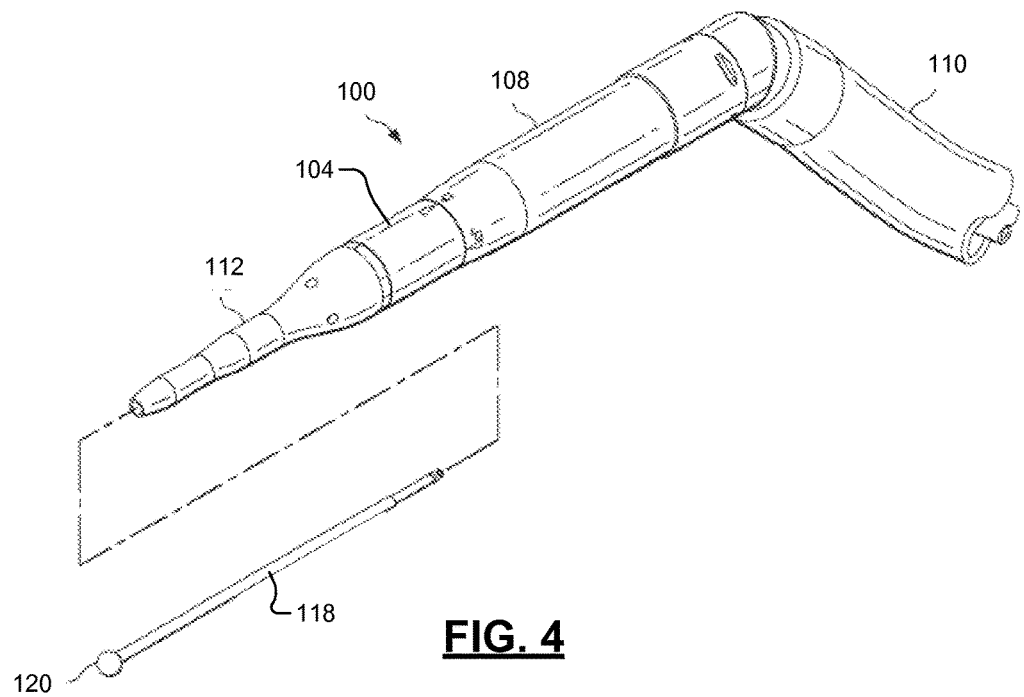
FIG. 4 is a perspective view of the surgical dissection cutter assembly of FIG. 3.

FIG. 4 is a perspective view of the surgical dissection cutter assembly 100. The dissection tool driver 104 includes a motor housing 108 connected to a hose or cable assembly 110. The hose assembly 110 supplies external power and control for the motor housing 108. The dissection tool driver 104 further includes an attachment housing 112 that connects to a dissection tool 118. A distal end of the dissection tool 118 includes a surgical bur 120. Examples of dissection tools that may be used in replacement of the dissection tool 118 are shown and described below with reference to FIGS. 6-10.

Figure 5:
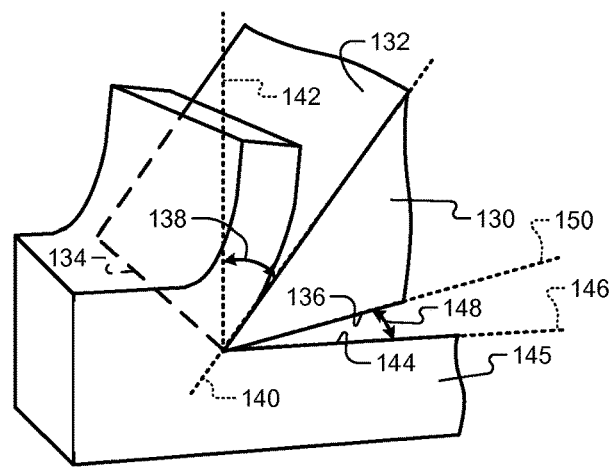
FIG. 5 is a perspective view of a portion of a surgical bur illustrating a rake angle and a relief angle.

FIG. 5 is a perspective view of a portion 130 of a surgical bur. The portion 130 includes a rake face 132 with a cutting edge 134 and a relief surface 136. The cutting edge 134 may be at a distal end of the surgical bur and adjacent to the relief surface 136. FIG. 5 is provided as an example and may be used to describe, for (i) an axial rake angle and axial relief surface of a cutting edge of a first rake surface, or (ii) a radial rake angle and a radial relief surface of a cutting edge of a second rake surface. The first rake surface may be the same or different than the second rake surface. Depending upon whether the surgical bur is being used for axial drilling or radial side cutting, the surgical bur may be in a different orientation relative to a cutting surface. A first orientation may be used for axial drilling and a second orientation may be used for radial side cutting.

If FIG. 5 is used to show the first orientation, an axial rake angle and an axial relief surface, a rake angle 138 (may be referred to as an axial rake angle for the first orientation) of the rake face 132 may be between (i) a line (or plane) 140 on the rake face 132 and a plane perpendicular to the cutting edge 134 and (ii) a line (or plane) 142 extending perpendicular to a surface 144 of a bone 145 into which the surgical bur is cutting and extending in a direction of the cut and/or a line (or plane) 146 perpendicular to line 142. A relief angle 148 (may be referred to as an axial relief angle for the first orientation) may be between (i) a line (or plane) 150 on the relief surface 136 (or axial relief surface 136 for the first orientation) and a plane perpendicular to the cutting edge 134 and (ii) the line 146. The cutting edge 134 may be on a plane perpendicular to the line 142 for the first orientation. The rotational axis of the surgical bur is parallel to line 142 for the first orientation.

If FIG. 5 is used to show the second orientation, a radial rake angle and a radial relief surface, the line 142 may be perpendicular to the longitudinal axis of the surgical bur. The cutting edge 134 may be in a plane that passes through the longitudinal axis. For the second orientation, the cutting edge 134 may be the same or a different cutting edge than the cutting edge referred to above for the first orientation. The relief surface 136 may be referred to as a radial relief surface for the second orientation. The rake angle 138 may be referred to as a radial rake angle for the second orientation. The relief angle 148 may be referred to as an axial relief angle for the second orientation.

Although the following surgical burs are shown as having a particular number of flutes, rake surfaces per flute, rake angles per flute, clearance surfaces per flute, lands, axial relief surfaces, clearance surfaces, etc., the surgical burs may have other quantities of each of these items.

Figure 6:
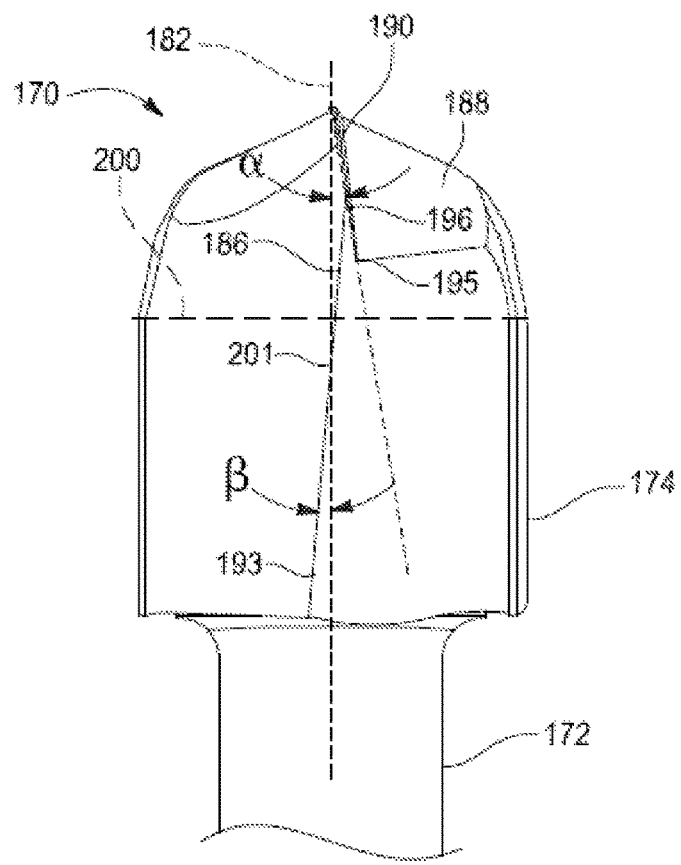
FIG. 6 is a side view of a dissection tool including a surgical bur in accordance with an embodiment of the present disclosure.
Figure 7:
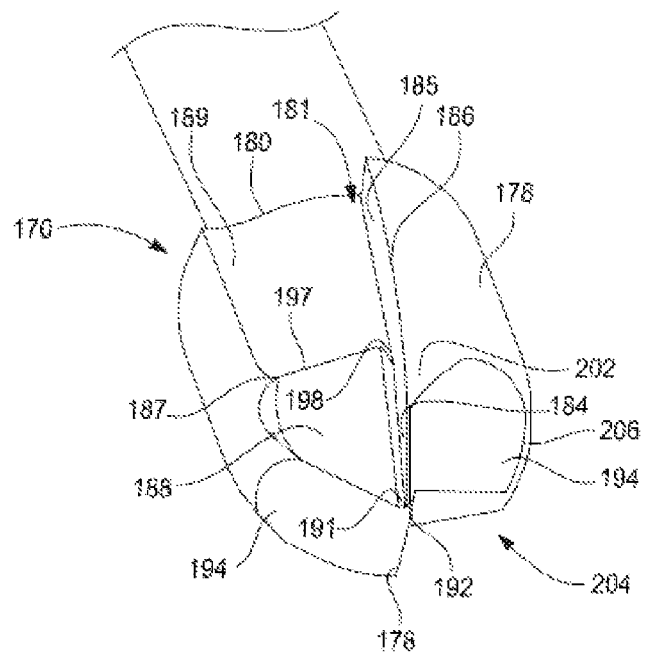
FIG. 7 is a perspective view of the dissection tool of FIG. 6.

FIGS. 6-7 show side and perspective views of a dissection tool 170. The dissection tool 170 may be used as part of the assembly 100 of FIG. 3 and replace the dissection tool 108 of FIG. 4. The dissection tool 170 includes a shaft 172 and a surgical bur 174. The surgical bur 174 has a "match head" design and includes a body 176. The surgical bur 174 may be referred to as a "neuro" or "matchstick" bur. The body 176 has two convex lands 178 and two flutes 180. Each of the flutes 180 is located between the lands 178 and has a corresponding chip space 181. The lands 178 are convex-shaped and/or rounded and may be in respective 180° locations about a longitudinal axis 182 of the dissection tool 170, the shaft 172, and/or the surgical bur 174. The surgical bur is rotated about the longitudinal axis 182. The flutes 180 may also be in respective 180° locations about the longitudinal axis 182. Each of the flutes 180 has two or more rake surfaces (two rake surfaces 184, 185 per flute 180 are shown) with a cutting edge 186 and corresponding clearance surfaces 187 with distal portions (or distal clearance surfaces) 188 and proximal portions (or proximal clearance surfaces) 189. The clearance surfaces 188 are on distal portions of the flutes 180. The clearance surfaces 189 are on proximal portions of the flutes 180.

In the example shown, first portions 190 of the cutting edges 186 extend from a center point 191 or bridge 192 at a distal end of the surgical bur 174, radially away from the longitudinal axis 182, and towards second portions 193 of the cutting edges 186. The bridge 192 extends over the center point 192 and connects axial relief surfaces 194 on respective ones of the lands 178.

The second portions 193 of the cutting edges 186 extend from proximal ends of the first portions 190 and axially along the longitudinal axis 182. The first portions 190 of the cutting edges 186 have negative axial rake angles. The left-hand (or negative) axial angle α is shown and creates the negative axial rake angle. As an example, a negative axial rake angle may be −5° or other suitable negative axial rake angle. The second portions 193 of the cutting edges 186 have positive radial rake angles proximal from point 201. An example right-hand (or positive) axial angle β is shown and creates the radial rake angles when manifested with location of point 201. As an example, a right-hand axial angle may be 5° or other suitable axial angle. As an example, the radial rake angles may vary from −5° at point 196 to 5° at the proximal end of the second portions 193.

Figure 10:
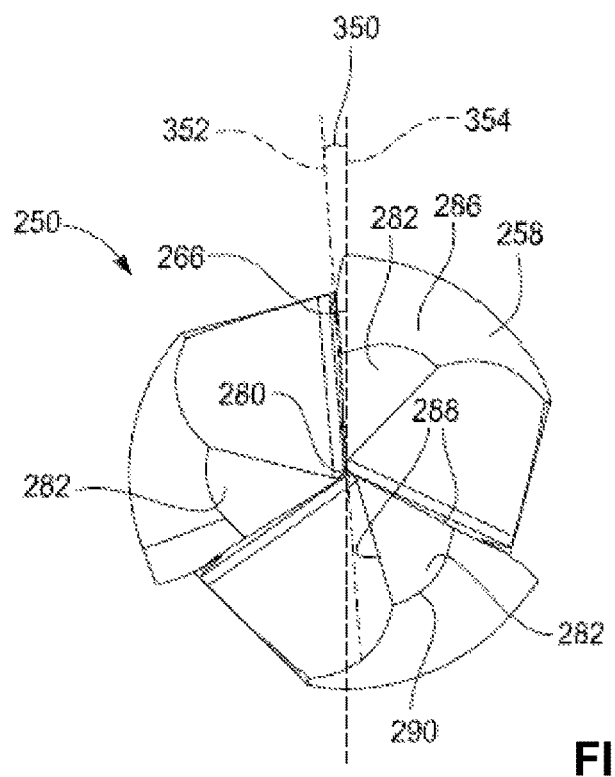
FIG. 10 is a distal end view of the surgical bur of the dissection tool of FIG. 8.

Axial rake angles affect cutting performance when drilling in a distal direction. The portion 190 is primarily used when drilling in the distal direction. The axial rake angles, of concern when drilling in a distal direction, are measured between a plane perpendicular to the longitudinal axis 182 and a plane on the distal rake face 184 and when viewed from a side of the surgical bur, as shown in FIG. 6. Radial rake angles affect cutting performance in a lateral direction. Some of the portion 190 and/or some of the portion 193 may be used when cutting in a lateral direction. A lateral direction refers to a direction away from the longitudinal axis 182. The lateral direction may not necessarily be a direction perpendicular to the longitudinal axis. The radial rake angles are measured between the longitudinal axis 182 and the respective portions 190, 193 of the cutting edges 186. The radial rake angles may be measured from a respective side of the surgical bur 174 and in a direction perpendicular to the longitudinal axis 182 and passing through a point on the cutting edges 186. The radial rake angles may also be measured from a distal end of the surgical bur 174 and/or at lateral cross-sectional planes of the surgical bur. The lateral cross-sectional planes of the surgical bur 174 being at points along the longitudinal axis 182 and the cutting edges 186. An example of a radial rake angle as measured from a distal end of a surgical bur is shown in FIG. 10.

The radial rake angle at a point on the cutting edges 186 may be described as being negative when that point is before (or to the right of) the longitudinal axis 182, as depicted in FIG. 6. The radial rake angle is neutral at points 201 where the second portions 193 cross the longitudinal axis 182. The radial rake angle at a point on the cutting edges 186 may be described as being positive when that point is after (or to the left of) the longitudinal axis 182, as depicted in FIG. 6. The first portions 190 and the second portions 193 of the cutting edges 186 may each be in a respective plane.

The axial and radial rake angles of the rake surfaces 184, 185 of each of the flutes 180 are decoupled. This is because: the axial rake angles of the rake surfaces 184, 185 of each of the flutes 180 are different and have different vertices; and/or the radial rake angles of the rake surfaces 184, 185 of each of the flutes 180 are different and have different vertices. The radial rake angles of each of the rake surfaces 184, 185 of each of the flutes 180 may not be constant along a corresponding cutting edge. In one implementation, each of the rake surfaces 184, 185 may have one or more (or a set) of radial rake angles. As an example, each of the rake surfaces 184, 185, corresponding to the portions 193 and located between a proximal end of the surgical bur 174 and second points 196, has multiple radial rake angles including a negative radial rake angle distal of the point 201, a neutral radial rake angle at the point 201, and a positive radial rake angle proximal of the point 201.

The first portions 190 of the cutting edges 186 may begin at or near the center point 191 and end at first points 195 proximal to the second points 196. The first points 195 refer to where distal ends of the first rake surfaces 184 and distal ends of the clearance surfaces 188 meet. When the surgical bur 174 is viewed from the side as shown and as described above, each of the first points 195 is on a corresponding first side of the longitudinal axis 182. The second points 196 refer to locations at which the first portions 190 of the cutting edges 186 meet the second portions 193 of the cutting edges 186. When the surgical bur 174 is viewed from the side as shown and as described above, each of the second portions 193 of the cutting edges 186 begins at a respective one of the second points 196 on the respective first side of the longitudinal axis 182 and extends across the longitudinal axis 182 to a respective second side of the longitudinal axis 182.

The cutting edges 186 provide a combination of right-hand axial and left-hand axial aspects with respect to the longitudinal axis 182. The first portions 190 of the cutting edges 186 are shown as providing left-hand axial aspects. For this reason, distal portions of the flutes 180 are referred to as left-hand portions. The second portions 193 of the cutting edges 186 are shown as providing right-hand axial aspects. For this reason, proximal portions of the flutes 180 are referred to as right-hand portions. The left-hand and right-hand axial aspects are provided for a surgical bur designed to be rotated in a clockwise direction about a longitudinal axis, as viewed from a proximal end of the surgical bur, to drill and/or cut. For a surgical bur designed to be rotated in a counter clockwise direction about a longitudinal axis, as viewed from a proximal end of the surgical bur, to drill and/or cut, (i) the first portions 190 may be opposite that shown and provide right-hand axial aspects, and (ii) the second portions 193 may be opposite that shown and provide left-hand axial aspects.

The clearance surfaces 188, 189 may each be flat (or planar), as shown, or may be curved. A transition edge 197 may extend laterally between the clearance surfaces 188, 189 of each of the flutes 180 and away from a corresponding one of the second rake surfaces 185. The clearance surfaces 188, 189 are at different angles relative to the longitudinal axis 182 and are in contact with each other at the transition edge 197. Each of the transition edges 197 borders and provides a transition between the corresponding clearance surfaces 188, 189.

For each of the flutes 180, the rake surfaces 184, 185 are decoupled and as a result are not continuous with each other. The rake surfaces 184, 185 of each of the flutes 180 may be distinct planar surfaces and are not parallel to each other. Due to the decoupling of the rake surfaces 184, 185, each of the clearance surfaces 189 may include a decoupling area 198 located between two of the corresponding rake surfaces 184, 185. The decoupling areas 198 extend axially and/or generally along the longitudinal axis 182 from the second points 196 to distal ends of the second clearance surfaces 189. Distal ends of the decoupling areas 198 are laterally in alignment with the decoupling edges 197. The first rake surfaces 184 meet the second rake surfaces 185 at the second points 196. The decoupling areas 198 separate proximal ends of the first rake surfaces 184 from distal ends of the second rake surfaces 185.

Depths (i.e. distances between the first portions 190 of the cutting edges to the clearance surfaces 188) of the first rake surfaces 184 may increase from distal ends of the first rake surfaces 184 to the corresponding points 196. Depths of the first rake surfaces 184 may decrease from the points 196 to the points 195. Depths (i.e. distances between the second portions 193 of the cutting edges to the clearance surfaces 189) of the second rake surfaces 185 may increase from distal ends of the second rake surfaces 185 and/or the points 196 to an equator (a planar second of the surgical bur 174 shown by a dashed line 200) and/or proximal ends of the second rake surfaces 185.

The equator 200 may refer to planar portion of the surgical bur 174 that is perpendicular to the longitudinal axis 182 and may be where a diameter of the surgical bur 174 is at a maximum. If the surgical bur has a constant diameter for an extended portion of the surgical bur, as in the example shown, the equator may be at the most distal portion of the surgical bur, which has the maximum diameter. The equator 200 may be (i) distal to the points 201 at which the second portions 193 of the cutting edges 186 cross the longitudinal axis 182, and (ii) proximal to the first points 195.

The rake surfaces 184, 185 and the respective portions 190, 193 of the cutting edges 186 decouple the rake angles of the portions 190, 193 and have respective functions. The first portions 190 of the cutting edges 186 are at distal ends of the flutes 180 to provide stability during drilling. Due to the decoupling of the rake surfaces 184, 185, the first portions 190 of the cutting edges 186 minimally or do not negatively affect side cutting or shaving when using the second portions 193 of the cutting edges 186. The second portions 193 of the cutting edges 186 extend along sides of the body 176 and in distal and proximal directions away from the equator 200. The second portions 193 of the cutting edges 186 provide efficient side cutting or shaving. Due to the decoupling of the rake surfaces 184, 185, the second portions 193 of the cutting edges 186 minimally or do not negatively affect drilling when using the first portions 190 of the cutting edges 186.

The surgical bur 174 includes a drill point 204 at a distal end of the surgical bur 174. The drill point 204 may include the center point 191 and the axial relief surfaces 194. The longitudinal axis 182 passes through the center point 191. The axial relief surfaces 194 are at ends of the flutes 180 and may be continuous with the lands 178 or may be distinct from the lands 178, as shown. The axial relief surfaces 194, as shown, are distinct from the lands 178 because: the axial relief surfaces 194 are a different type of surface than the lands (e.g., the lands 178 may be convex-shaped and the axial relief surfaces 194 may be planar-shaped); and there are transitional surfaces or edges (referred to as borders) between the axial relief surfaces 194 and the lands 178. In another embodiment, the axial relief surfaces 194 may be convex-shaped and/or provide a non-transitional (or continuous surface) with the lands 178.

Each of the axial relief surfaces 194 are bordered by (i) one of the first portions 190 of one of the cutting edges 186, (ii) a distal end portion 202 of one of the lands 178, and (iii) one of the clearance surfaces 188. The axial relief surfaces 194 may be flat (or planar) surfaces, as shown. Each of the axial relief surfaces 194 may have two nominally straight edges (the first portions 190 and the distal edges of the clearance surfaces 188) connected by a respective circular edge (one of the curved edges is identified by numerical designator 206). The curved edges 206 of the axial relief surfaces 194 border respectively the lands 178.

The clearance (or distal) surfaces 188 have corresponding gash angles. Each of the gash angles refers to an angle between (i) a line (or plane) extending parallel to and on one of the distal surfaces 188 and away from the center point 191 and/or the longitudinal axis 182 and (ii) a line (or plane) extending perpendicular to the longitudinal axis 182.

Figure 8:
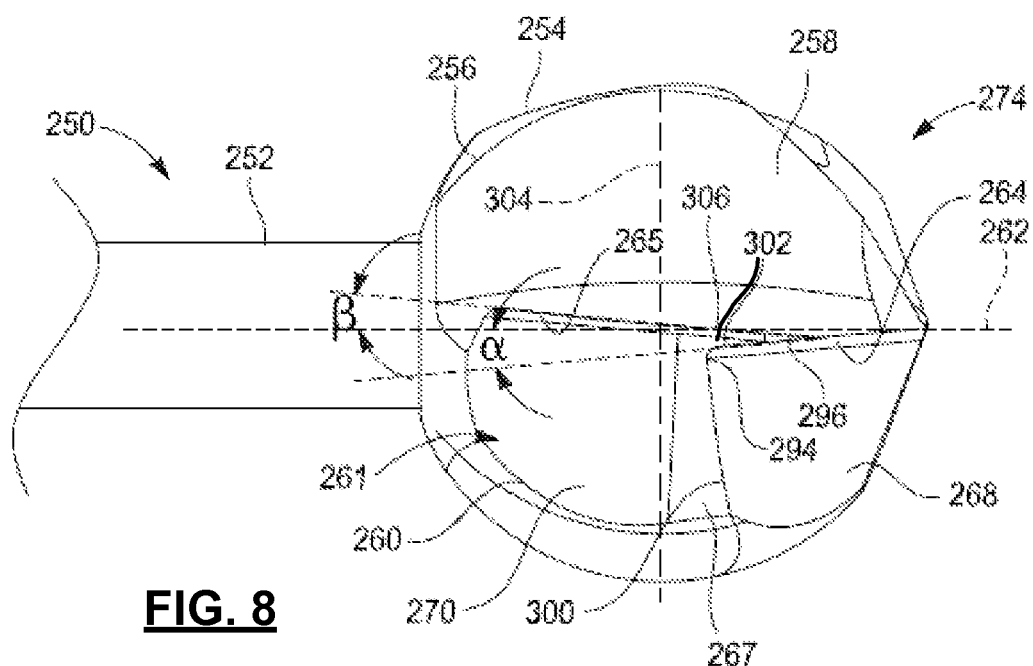
FIG. 8 is a side view of another dissection tool including another surgical bur in accordance with an embodiment of the present disclosure and taken opposite to a clearance surface of a flute of the surgical bur.
Figure 9:
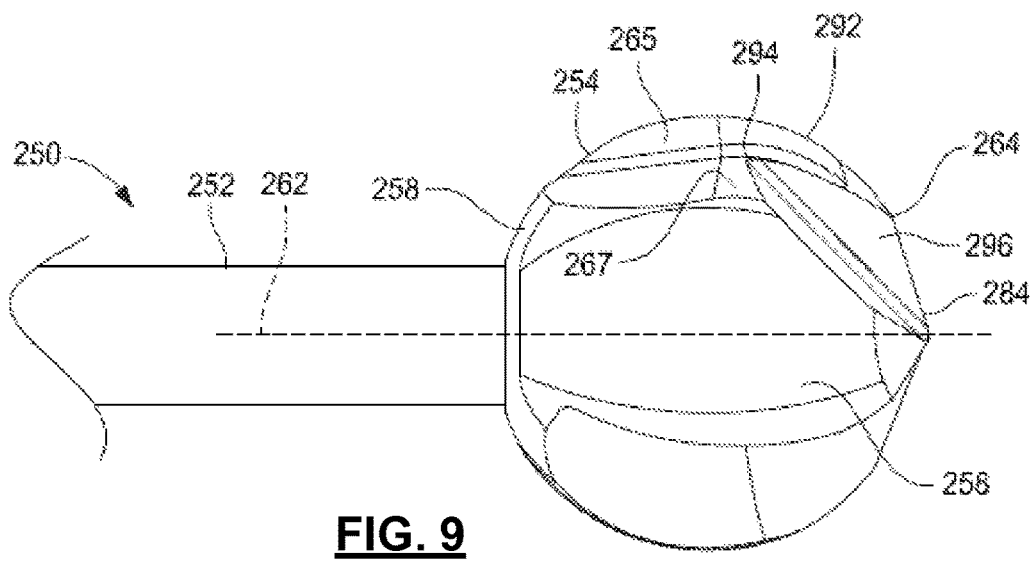
FIG. 9 is another side view of the surgical tool of FIG. 8 rotated 90° clockwise from the position shown in FIG. 8 and taken opposite certain rake surfaces of the surgical bur.

FIGS. 8-10 show side and perspective views of a dissection tool 250. FIG. 8 shows a lateral side view of the dissection tool 250 taken from a left side when looking at FIG. 10. FIG. 9 shows a lateral side (or top) view of the dissection tool 250 taken from above the dissection tool when looking at FIG. 10. The dissection tool 250 may be used as part of the assembly 100 of FIG. 3 and replace the dissection tool 108 of FIG. 4. The dissection tool 250 includes a shaft 252 and a spherically-shaped surgical bur 254. The surgical bur 254 includes a body 256. The body 256 has three convex-shaped lands 258 and three flutes 260. Each of the flutes 260 is located between a pair of the lands 258 and has a corresponding chip space 261. The lands 258 are convex-shaped and/or rounded and may be in respective 120° locations about a longitudinal axis 262 of the dissection tool 250, the shaft 252, and/or the surgical bur 254. The surgical bur is rotated about the longitudinal axis 262. The flutes 260 may also be in respective 120° locations about the longitudinal axis 262. Each of the flutes 260 has distal and proximal rake surfaces (or faces) 264, 265 with a cutting edge 266 and clearance surfaces 267. The clearance surfaces 267 include distal portions (or distal clearance surfaces) 268 and proximal portions (or proximal clearance surfaces) 269. The clearance surfaces 268 are on distal portions of the flutes 260. The clearance surfaces 269 are on proximal portions of the flutes 260.

The surgical bur 254 includes a drill point 274 at a distal end of the surgical bur 254. The drill point 274 may include a center point 280 and three axial relief surfaces 282. The longitudinal axis 262 passes through the center point 280. The axial relief surfaces 282 are at ends of the flutes 260 and may be distinct from the lands 258. The axial relief surfaces 282 may be distinct from the lands 258 because: the axial relief surfaces 282 are a different type of surface than the lands (e.g., the lands 258 may be convex-shaped and the axial relief surfaces 282 may be planar-shaped); and there are transitional surfaces (or borders) between the axial relief surfaces 282 and the lands 258. In another embodiment, the axial relief surfaces 282 may be convex-shaped and/or provide a non-transitional (or continuous surface) with the lands 258.

Each of the axial relief surfaces 282 are bordered by (i) a respective distal end (or first) portion 284 of one of the cutting edges 266, (ii) a distal end portion 286 of one of the lands 258, and (iii) a distal end of one of the clearance surfaces 268. The axial relief surfaces 282 may be flat (or planar) surfaces, as shown. Each of the axial relief surfaces 282 are triangular-shaped with two nominally straight edges (two of the nominally straight edges are identified by numerical designator 288) and a curved edge (one of the curved edges is identified by numerical designator 290). The curved edges 290 of the axial relief surfaces 282 border respectively the lands 258.

In the example shown, the first portions 284 of the cutting edges 266 extend from the center point 280 at a distal end of the surgical bur 254, radially away from the longitudinal axis 262, and towards second portions 292 of the cutting edges 266. The second portions 292 of the cutting edges 266 extend from proximal ends of the first portions 284 and axially along the longitudinal axis 262. The first portions 284 of the cutting edges 266 have negative axial rake angles. An example left-hand axial angle α is shown and creates the negative axial rake angle. As an example, a negative axial rake angle may be −5° or other suitable negative axial rake angle. The second portions 292 of the cutting edges 266 have positive radial rake angles proximal from point 306. An example axial angle β is shown and creates the radial rake angles when manifested with location of point 306. As an example, a right-hand axial angle may be 5° or other suitable axial angle. As an example, the radial rake angles may vary from −2° near point 296 to 5° at the proximal end of the second portions 292.

The axial rake angles are measured between a plane perpendicular to the longitudinal axis 262 and a plane on the distal rake face. The radial rake angles are measured between the longitudinal axis 262 and the respective portions 284, 292 of the cutting edges 266. These measurements are taken from a respective side of the surgical bur 254 and in a direction perpendicular to the longitudinal axis 262 and passing through a point on the cutting edges 266. The first portions 284 and the second portions 292 of the cutting edges 266 may each be in a respective plane.

The rake angles of each of the flutes 260 are decoupled since the rake angles are different, have different vertices, and are associated with different rake surfaces. The vertices of the axial rake angles may be at the same point (e.g., the center point 280). The vertices of the radial rake angles are different and refer to points (e.g., the point 306) where the second portions 292 of the cutting edges 266 cross the longitudinal axis 262.

The first portions 284 of the cutting edges 266 may begin at or near the center point 280 and end at first points 294 proximal to second points 296. The first points 294 refer to where distal ends of the first rake surfaces 264 and distal ends of the clearance surfaces 268 meet. When the surgical bur 254 is viewed from the side as shown and as described above, each of the first points 294 is on a corresponding first side of the longitudinal line 262. The second points 296 refer to locations at which the first portions 284 of the cutting edges 266 meet the second portions 292 of the cutting edges 266. When the surgical bur 254 is viewed from the side as shown and as described above, each of the second portions 292 of the cutting edges 266 begins at a respective one of the second points 296 on the respective first side of the longitudinal axis 262 and extends across the longitudinal axis 262 to a respective second side of the longitudinal axis 262.

The cutting edges 266 provide a combination of right-hand axial and left-hand axial aspects with respect to the longitudinal axis 262. When viewed from the side (as shown in FIG. 8), the cutting edges 266 extend along the longitudinal axis 262, from above the longitudinal axis 262 at a proximal end of the surgical bur 254, to the second points 296 at locations below the longitudinal axis 262, and generally back up to the longitudinal axis 262 at the center point 280. The first portions 284 of the cutting edges 266 are shown as providing left-hand axial aspects. For this reason, distal portions of the flutes 260 are referred to as left-hand portions. The second portions 292 of the cutting edges 266 are shown as providing right-hand axial aspects. For this reason, proximal portions of the flutes 260 are referred to as right-hand portions. The left-hand and right-hand axial aspects are provided for a surgical bur designed to be rotated in a clockwise direction about a longitudinal axis, as viewed from a proximal end of the surgical bur, to drill and/or cut. For a surgical bur designed to be rotated in a counter clockwise direction about a longitudinal axis, as viewed from a proximal end of the surgical bur, to drill and/or cut, (i) the first portions 284 may be opposite that shown and provide right-hand axial aspects, and (ii) the second portions 292 may be opposite that shown and provide left-hand axial aspects.

The clearance surfaces 268, 270 may each be flat (or planar), as shown, or may be curved. A transition edge 300 may extend laterally between the clearance surfaces 268, 270 of each of the flutes 180 and away from a corresponding one of the second rake surfaces 265. The clearance surfaces 268, 270 are at different angles relative to the longitudinal axis 262 and are in contact with each other at the decoupling edge 300. Each of the transition edges 300 borders and provides a transition between the corresponding clearance surfaces 268, 270.

For each of the flutes 260, the rake surfaces 264, 265 are decoupled and as a result are not continuous with each other. The rake surfaces 264, 265 of each of the flutes 260 may be distinct planar surfaces and are not parallel to each other. Due to the decoupling of the rake surfaces 264, 265, each of the clearance surfaces 268, 270 may include a decoupling area 302 located between two of the corresponding rake surfaces 264, 265. The decoupling areas 302 extend axially and/or generally along the longitudinal axis 262 from the second points 296 to distal ends of the clearance surfaces 270. Distal ends of the decoupling areas 302 are laterally in alignment with the transition edges 300. The first rake surfaces 264 meet the second rake surfaces 265 at the second points 296. The decoupling areas 302 separate proximal ends of the first rake surfaces 264 from distal ends of the second rake surfaces 265.

Depths (i.e. distances between the first portions 284 of the cutting edges 266 to the clearance surfaces 268) of the first rake surfaces 264 may increase from distal ends of the first rake surfaces 264 to the corresponding points 296. Depths of the first rake surfaces 264 may decrease from the points 296 to the points 294. Depths (i.e. distances between the second portions 292 of the cutting edges 266 to the clearance surfaces 270) of the second rake surfaces 265 may increase from distal ends of the second rake surfaces 265 and/or the points 296 to an equator (a midline or planar section of the surgical bur 254 shown by a dashed line 304) and/or proximal ends of the second rake surfaces 265.

The equator 304 may refer to planar portion of the surgical bur 174 that is perpendicular to the longitudinal axis 262 and may be where a diameter of the surgical bur 254 is at a maximum. The equator 304 is (i) proximal to the points 306 at which the second portions 292 of the cutting edges 266 cross the longitudinal axis 262, and (ii) proximal to the first points 294.

The rake surfaces 264, 265 and the respective portions 284, 292 of the cutting edges 266 decouple the rake angles of the portions 284, 292 and have respective functions. The first portions 284 of the cutting edges 266 are at distal ends of the flutes 260 to provide stability during drilling. Due to the decoupling of the rake surfaces 264, 265, the first portions 284 of the cutting edges 266 minimally or do not negatively affect side cutting or shaving when using the second portions 292 of the cutting edges 266. The second portions 292 of the cutting edges 266 extend along sides of the body 256 and in distal and proximal directions away from the equator 304. The second portions 292 of the cutting edges 266 provide efficient side cutting or shaving. Due to the decoupling of the rake surfaces 264, 265, the second portions 292 of the cutting edges 266 minimally or do not negatively affect drilling when using the first portions 284 of the cutting edges 266.

The clearance (or distal) surfaces 268 have corresponding gash angles. Each of the gash angles refers to an angle between (i) a line (or plane) extending parallel to and on one of the distal surfaces 268 and away from the center point 280 and/or the longitudinal axis 262 and (ii) a line (or plane) extending perpendicular to the longitudinal axis 262.

Each of the rake surfaces 264 has a corresponding radial rake angle 350. A radial rake angle 350 refers to an angle between (i) a line (or plane) 352 parallel to one of the rake surfaces 264 and (ii) a line (or plane) 354 passing through the second portions 292 of the cutting edge 266 and the longitudinal axis 262. Radial rake angles 250 of the rake surfaces 264 may be associated with a left-hand helix with respect to the longitudinal axis 262 corresponding to the left-hand axial aspects of the rake surfaces 264.

The above-disclosed implementations include surgical bur configurations designed to drill, cut and shape bone efficiently while allowing contact with sensitive soft tissue structures (e.g., nerves, blood vessels, membranes, etc.) without tearing the soft tissue structures. This is especially applicable in neurological and spinal procedures where the dura mater can be exposed to a distal portion of a bur.

In certain implementations, rake angles of the surgical burs may also be within predetermined ranges and based on the application of use.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical bur comprising:
   a plurality of flutes, wherein each of the plurality of flutes comprises a cutting edge;
   a plurality of rake surfaces;
   a planar clearance surface,
   wherein the plurality of rake surfaces of one of the flutes comprises
      a first rake surface having a first rake angle and a first distinct planar surface, and
      a second rake surface having a second rake angle and a second distinct planar surface, wherein the second rake angle is decoupled from the first rake angle, and wherein the first rake surface and the second rake surface are distinct from the planar clearance surface; and
   a plurality of lands, wherein each of the plurality of lands is disposed between a pair of the plurality of flutes;
   wherein:
      the first rake surface of the one of the flutes has a negative axial rake angle; and
      the second rake surface of the one of the flutes has a positive radial rake angle.

2. The surgical bur of claim 1, wherein:
   the first rake surface of the one of the flutes and a first corresponding portion of one of the cutting edges are configured for drilling in a direction parallel or along a longitudinal axis of the surgical bur; and
   the second rake surface of the one of the flutes and a second corresponding portion of the one of the cutting edges are configured for cutting in a radial or lateral direction relative to the longitudinal axis of the surgical bur.

3. The surgical bur of claim 1, wherein the plurality of rake surfaces of the one of the plurality of flutes are decoupled from each other.

4. The surgical bur of claim 1, wherein:
   the first rake surface has a first vertex and a first corresponding portion of one of the cutting edges, wherein a depth of the first rake surface increases in size from a distal end of the first rake surface to the first vertex; and
   the second rake surface has a second vertex, wherein a depth of the second rake surface increases in size from the second vertex to (i) an equator of the surgical bur, (ii) a proximal end of the second rake surface, (iii) a proximal end of the surgical bur, or (iv) a proximal end of the one of the plurality of flutes.

5. The surgical bur of claim 1, wherein:
   one of the plurality of flutes comprises a decoupling area; and
   the decoupling area is located between the first rake surface and the second rake surface.

6. The surgical bur of claim 1, wherein:
   each of the plurality of flutes comprises a respective decoupling area; and
   each of the decoupling areas is located between two of the plurality of rake surfaces of the respective one of the plurality of flutes.

7. The surgical bur of claim 1, wherein:
   the plurality of flutes comprise respective first rake surfaces and respective second rake surfaces, wherein, for each of the plurality of flutes, the first rake surface meets the second rake surface at a respective point;
   each of the second rake surfaces comprising a respective vertex; and
   wherein, for each of the plurality of flutes, a proximal point or end of each of the first rake surfaces is at the respective vertex of the corresponding second rake surface.

8. The surgical bur of claim 1, further comprising a drill point comprising a plurality of axial relief surfaces, wherein each of the plurality of axial relief surfaces borders (i) a distal portion of a respective one of the cutting edges, (ii) a respective one of the lands, and (iii) a respective one of the planar clearance surfaces.

9. A surgical bur comprising:
   a plurality of flutes, wherein each of the plurality of flutes comprises a cutting edge, a plurality of rake surfaces and a planar clearance surface,
   wherein
      the plurality of rake surfaces of one of the plurality of flutes includes at least a first rake surface and a second rake surface,
      the first rake surface has a first distinct planar surface,
      the second rake surface has a second distinct planar surface,
      the first rake surface and the second rake surface are decoupled from each other, and
      the first rake surface and the second rake surface are distinct from the planar clearance surface; and a plurality of lands, each of the plurality of lands is disposed between a pair of the plurality of flutes;
wherein the one of the plurality of flutes comprises:
the first rake surface having a first axial angle; and
the second rake surface having a second axial angle, wherein one of the first axial angle and the second axial angle is a positive axial angle relative to a longitudinal axis of the surgical bur, and wherein the other one of the first axial angle and the second axial angle is a negative axial angle relative to the longitudinal axis.

10. The surgical bur of claim 9, wherein the plurality of rake surfaces of the one of the plurality of flutes comprises:
the first rake surface; and
the second rake surface having a different rake angle than the first rake surface.

11. The surgical bur of claim 10, wherein the first rake surface or the second rake surface has a plurality of radial rake angles.

12. The surgical bur of claim 10, wherein each of the first rake surface and the second rake surface has a plurality of radial rake angles.

13. The surgical bur of claim 10, wherein the first rake surface or the second rake surface includes a negative radial rake angle, a neutral radial rake angle and a positive radial rake angle.

14. The surgical bur of claim 10, wherein:
the first rake surface or the second rake surface comprises a plurality of radial rake angles; and
the plurality of radial rake angles have different vertices.

15. The surgical bur of claim 9, wherein each of the plurality of lands is convex-shaped.

16. The surgical bur of claim 9, wherein:
the plurality of rake surfaces of each of the plurality of flutes are decoupled from each other;
each of the plurality of flutes comprises a respective decoupling area; and
each of the decoupling areas is located between two of the plurality of rake surfaces of the corresponding one of the plurality of flutes.

17. The surgical bur of claim 9, wherein the plurality of rake surfaces of each of the plurality of flutes meet at a respective point.

18. The surgical bur of claim 9, wherein the plurality of rake surfaces of each of the plurality of flutes comprises:
the first rake surface; and
the second rake surface comprising a vertex,
wherein, for each of the plurality of flutes, a proximal point or end of each of the first rake surfaces is at the respective vertex of the corresponding second rake surface.

19. The surgical bur of claim 9, wherein the plurality of rake surfaces in each of the plurality of flutes are in respective planes and are at different angles relative to a longitudinal axis of the surgical bur.

20. The surgical bur of claim 9, wherein:
the first axial angle is a negative axial rake angle;
the second axial angle is a positive axial rake angle; and
the second rake surface is proximal to the first rake surface.

21. The surgical bur of claim 9, further comprising a drill point comprising a plurality of axial relief surfaces, wherein each of the plurality of axial relief surfaces borders (i) a distal portion of a respective one of the cutting edges, (ii) a respective one of the lands, and (iii) a respective one of the planar clearance surfaces.

22. The surgical bur of claim 21, wherein each of the plurality of axial relief surfaces has a planar area and is distinct from the lands.

23. The surgical bur of claim 9, wherein:
the first rake surface has a first constant radial rake angle along a corresponding cutting edge of the surgical bur; and
the second rake surface has a second constant radial rake angle along the corresponding cutting edge of the surgical bur.

24. The surgical bur of claim 9, wherein:
the first rake surface is a planar surface; and
the second rake surface is a planar surface.

25. The surgical bur of claim 9, wherein:
the second rake surface extends longitudinally along a portion of the cutting edge; and
the portion of the cutting edge extends longitudinally along one of the plurality of lands.

26. The surgical bur of claim 9, further comprising an axial relief surface, wherein:
the first rake surface and the second rake surface meet at a decoupling point; and
the decoupling point is more proximally located on the surgical bur than the axial relief surface.

27. The surgical bur of claim 9, wherein the surgical bur is a match head style surgical bur.

28. The surgical bur of claim 9, wherein the surgical bur is spherically-shaped.

29. The surgical bur of claim 9, wherein the second rake surface is at least partially located proximal to the first rake surface and is decoupled from the first rake surface, such that while the surgical bur is in use, the second rake surface provides side cutting while not negatively affecting axially drilling provided by the first rake surface.

30. A surgical bur comprising:
a plurality of flutes, wherein each of the plurality of flutes comprises a cutting edge, a plurality of rake surfaces and a planar clearance surface,
wherein
the plurality of rake surfaces of one of the plurality of flutes includes at least a first rake surface and a second rake surface,
the first rake surface has a first distinct planar surface,
the second rake surface has a second distinct planar surface,
the first rake surface and the second rake surface are decoupled from each other, and
the first rake surface and the second rake surface are distinct from the planar clearance surface; and
a plurality of lands, each of the plurality of lands is disposed between a pair of the plurality of flutes;
wherein the one of the plurality of flutes comprises:
the first rake surface having a first vertex and a first corresponding portion of one of the cutting edges, wherein a depth of the first rake surface increases in size from a distal end of the first rake surface to the first vertex; and
the second rake surface having a second vertex, wherein a depth of the second rake surface increases in size from the second vertex to (i) an equator of the surgical bur, (ii) a proximal end of the second rake surface, (iii) a proximal end of the surgical bur, or (iv) a proximal end of the one of the plurality of flutes.

31. The surgical bur of claim 30, wherein the vertices of the first and second rake surfaces are at a same point.

32. The surgical bur of claim 30, wherein:
the one of the plurality of flutes comprises a decoupling area; and
the decoupling area is located between two of the plurality of rake surfaces of the one of the plurality of flutes.

33. A surgical bur comprising:
a plurality of flutes, wherein each of the plurality of flutes comprises a cutting edge;
a plurality of rake surfaces;
a planar clearance surface,
wherein the plurality of rake surfaces of one of the flutes comprises
    a first rake surface having a first rake angle and a first distinct planar surface, and
    a second rake surface having a second rake angle and a second distinct planar surface, wherein the second rake angle is decoupled from the first rake angle, and wherein the first rake surface and the second rake surface are distinct from the planar clearance surface; and
a plurality of lands, wherein each of the plurality of lands is disposed between a pair of the plurality of flutes;
wherein each of the cutting edges comprises:
    a first portion corresponding to one of the first rake surfaces, wherein the first portion is on a first side of a longitudinal axis of the surgical bur when the surgical bur is viewed from a side; and
    a second portion corresponding to one of the second rake surfaces and extending from and proximal to the corresponding one of the first portions, wherein the second portion crosses the longitudinal axis when the surgical bur is viewed from the side.

34. A surgical bur comprising:
a plurality of flutes, wherein each of the plurality of flutes comprises a cutting edge, a plurality of rake surfaces and a planar clearance surface,
wherein
    the plurality of rake surfaces of one of the plurality of flutes includes at least a first rake surface and a second rake surface,
    the first rake surface has a first distinct planar surface,
    the second rake surface has a second distinct planar surface,
    the first rake surface and the second rake surface are decoupled from each other, and
    the first rake surface and the second rake surface are distinct from the planar clearance surface; and
    a plurality of lands, each of the plurality of lands is disposed between a pair of the plurality of flutes;
wherein:
    the second rake surface extends longitudinally along a portion of the cutting edge; and
    the portion of the cutting edge extends longitudinally along one of the plurality of lands;
wherein depths of the second rake surface varies from a distal end of the second rake surface to a proximal end of the second rake surface.

35. A surgical bur comprising:
a plurality of flutes, wherein each of the plurality of flutes comprises a cutting edge, a plurality of rake surfaces and a planar clearance surface,
wherein
    the plurality of rake surfaces of one of the plurality of flutes includes at least a first rake surface and a second rake surface,
    the first rake surface has a first distinct planar surface,
    the second rake surface has a second distinct planar surface,
    the first rake surface and the second rake surface are decoupled from each other, and
    the first rake surface and the second rake surface are distinct from the planar clearance surface; and
    a plurality of lands, each of the plurality of lands is disposed between a pair of the plurality of flutes;
wherein:
    the second rake surface extends longitudinally along a portion of the cutting edge; and
    the portion of the cutting edge extends longitudinally along one of the plurality of lands;
further comprising an axial relief surface, wherein the first rake surface extends longitudinally along the axial relief surface.

36. The surgical bur of claim 35, wherein depths of the first rake surface varies from a distal end of the first rake surface to a proximal end of the first rake surface.

37. The surgical bur of claim 35, wherein the second rake surface is at least partially located proximal to the first rake surface.

38. The surgical bur of claim 35, wherein the axial relief surface extends along a distal edge of the one of the plurality of lands.

39. The surgical bur of claim 38, wherein the axial relief surface extends along a distal edge of the planar clearance surface.

40. The surgical bur of claim 35, wherein:
the axial relief surface is a planar surface; and
the one of the plurality of lands is convex-shaped.

41. A surgical bur comprising:
a plurality of flutes, wherein each of the plurality of flutes comprises a cutting edge, a plurality of rake surfaces and a planar clearance surface,
wherein
    the plurality of rake surfaces of one of the plurality of flutes includes at least a first rake surface and a second rake surface,
    the first rake surface has a first distinct planar surface,
    the second rake surface has a second distinct planar surface,
    the first rake surface and the second rake surface are decoupled from each other, and
    the first rake surface and the second rake surface are distinct from the planar clearance surface; and
    a plurality of lands, each of the plurality of lands is disposed between a pair of the plurality of flutes;
wherein:
    the planar clearance surface of the one of the plurality of flutes is a first planar clearance surface;
    the one of the plurality of flutes includes a second planar clearance surface decoupled from the first planar clearance surface;
    the first rake surface extends longitudinally along an edge of the first planar clearance surface; and
    the second rake surface extends longitudinally along an edge of the second planar clearance surface.

42. The surgical bur of claim 41, wherein the first planar clearance surface is distally located relative to the second planar clearance surface.

43. The surgical bur of claim 41, wherein a transitional edge extends laterally between the first planar clearance surface and the second planar clearance surface and away from the second rake surface.

* * * * *

UNITED STATES PATENT AND TRADEMARK OFFICE
CERTIFICATE OF CORRECTION

PATENT NO. : 10,335,166 B2  
APPLICATION NO. : 14/664258  
DATED : July 2, 2019  
INVENTOR(S) : John W. Kulas et al.

Page 1 of 1

It is certified that error appears in the above-identified patent and that said Letters Patent is hereby corrected as shown below:

On the Title Page

Line 1, Column 1, (73) Assignee, delete "MEDTRONICS" and insert --MEDTRONIC-- therefor In the Claims Column 11, Line 52, Claim 1, after "comprises", insert --:--

Column 12, Line 33, Claim 6, delete "areas" and insert --area-- therefor

Column 12, Line 57, Claim 9, after "wherein", insert --:--

Column 13, Line 39, Claim 16, delete "areas" and insert --area-- therefor

Column 14, Line 40, Claim 30, after "wherein", insert --:--

Column 15, Line 12, Claim 33, after "comprises", insert --:--

Column 15, Line 37, Claim 34, after "wherein", insert --:--

Column 15, Line 62, Claim 35, after "wherein", insert --:--

Column 16, Line 36, Claim 41, after "wherein", insert --:--

Signed and Sealed this  
Tenth Day of March, 2020

Andrei Iancu  
*Director of the United States Patent and Trademark Office*